US011634675B2

(12) United States Patent
Lee et al.

(10) Patent No.: US 11,634,675 B2
(45) Date of Patent: Apr. 25, 2023

(54) INSERTABLE CULTURE CONTAINER AND KIT FOR THREE-DIMENSIONAL CELL CULTURE, AND THREE-DIMENSIONAL CELL CO-CULTURE METHOD USING SAME

(71) Applicants: Korea Institute of Industrial Technology, Cheonan-si (KR); CEFO Co., Ltd., Seoul (KR)

(72) Inventors: Dongmok Lee, Daegu (KR); Hyunsook Park, Seoul (KR); Sunray Lee, Seoul (KR)

(73) Assignees: KOREA INSTITUTE OF INDUSTRIAL TECHNOLOGY, Cheonan-si (KR); CEFO CO., LTD., Seoul (KR)

( * ) Notice: Subject to any disclaimer, the term of this patent is extended or adjusted under 35 U.S.C. 154(b) by 431 days.

(21) Appl. No.: 16/770,663

(22) PCT Filed: Dec. 7, 2018

(86) PCT No.: PCT/KR2018/015569
§ 371 (c)(1),
(2) Date: Jun. 8, 2020

(87) PCT Pub. No.: WO2019/112391
PCT Pub. Date: Jun. 13, 2019

(65) Prior Publication Data
US 2021/0171888 A1 Jun. 10, 2021

(30) Foreign Application Priority Data
Dec. 8, 2017 (KR) .................. 10-2017-0168703

(51) Int. Cl.
C12M 1/00 (2006.01)
C12M 1/32 (2006.01)
C12N 5/00 (2006.01)

(52) U.S. Cl.
CPC ............ *C12M 23/02* (2013.01); *C12M 23/12* (2013.01); *C12N 5/0062* (2013.01); *C12N 2502/1382* (2013.01); *C12N 2513/00* (2013.01)

(58) Field of Classification Search
None
See application file for complete search history.

(56) References Cited

U.S. PATENT DOCUMENTS

2015/0050735 A1* 2/2015 Iyasere .................. C12M 25/06
435/395

FOREIGN PATENT DOCUMENTS

KR 10-2013-0131329 A 12/2013
KR 10-2017-0073686 A 6/2017
(Continued)

OTHER PUBLICATIONS

American National Standards Institute/Society for Laboratory Information and Screening. Publication Feb. 2004. (Year: 2011).*
(Continued)

*Primary Examiner* — Allison M Fox
*Assistant Examiner* — Jennifer S Spence
(74) *Attorney, Agent, or Firm* — NSIP Law (57) ABSTRACT

The present invention relates to an insertable culture container and a kit for three-dimensional cell culture, and a three-dimensional cell co-culture method using the same, the insertable culture container for three-dimensional cell culture comprising: a cylindrical side wall having open upper and lower portions; at least one hook protruding outward from the upper side of the side wall; and at least one support protruding inward from the lower side of the side wall. The present invention is advantageous in that air required for a three-dimensional cell culture structure can be smoothly supplied since the cell is cultured at a position spaced apart from a bottom surface of the culture container, (Continued)

and an existing culture plate can be used without change due to the culture container configured as an insert type.

7 Claims, 4 Drawing Sheets

(56) References Cited

FOREIGN PATENT DOCUMENTS

| WO | WO 2010/038013 A1 | 4/2010 | |
|---|---|---|---|
| WO | WO-2016069917 A1 * | 5/2016 | ............ C12M 23/12 |

OTHER PUBLICATIONS

Herroon et al. New 3D-culture approaches to study interactions of bone marrow adipocytes with metastatic prostate cancer cells. Frontiers in Endocrinology (2016) 7;84: 1-15. (Year: 2016).*

International Search Report dated Mar. 21, 2019 in corresponding International Patent Application No. PCT/KR2018/015569 (2 pages in English, 2 pages in Korean).

Riss, "Overview of 3D Cell Culture Model Systems and Factors to Consider When Choosing and Validating Cell-Based Assays for Use with 3D Cultures," Promega Corporation, Web Seminar Data, Mar. 2014, 2 pages.

Kämpfer et al., "Development of an in vitro co-culture model to mimic the human intestine in healthy and diseased state," Toxicology in Vitro, Aug. 12, 2017, vol. 45, pp. 31-43.

* cited by examiner

INSERTABLE CULTURE CONTAINER AND KIT FOR THREE-DIMENSIONAL CELL
CULTURE, AND THREE-DIMENSIONAL
CELL CO-CULTURE METHOD USING SAME

CROSS REFERENCE TO RELATED APPLICATIONS

This application is a U.S. National Stage Application of International Application No. PCT/KR2018/015569, filed on Dec. 7, 2018, which claims the benefit under 35 USC 119(a) and 365(b) of Korean Patent Application No. 10-2017-0168703, filed on Dec. 8, 2017 in the Korean Intellectual Property Office, the entire disclosure of which is incorporated herein by reference for all purposes.

TECHNICAL FIELD

The present invention relates to an insertable culture container and a kit for three-dimensional cell culture, and a three-dimensional cell co-culture method using the same, and more particularly, to an insertable culture container and a kit for three-dimensional cell culture, and a three-dimensional cell co-culture method using the same, in which air required for a three-dimensional cell culture structure can be smoothly supplied since the cells are cultured at a position spaced apart from a bottom surface of the culture container, and an existing culture plate can be used without change due to the culture container configured as an insert type, unlike the related art.

BACKGROUND ART

Cell culture is the most basic research method in the field of biotechnology, and is widely used not only for studying the function of living organisms but also for studying human diseases. Although more than 40 years have passed since the development and establishment of general eukaryotic cell culture methods, the most commonly used method to support the growth of adherent cells is to culture cells on a two-dimensional surface consisting of a substrate formed of a synthetic polymer resin such as polystyrene, polypropylene, polyethylene, and polycarbonate (PC), or glass.

However, cells grown by a two-dimensional cell culture method, which is a monolayer cell culture method, show many differences from cells that grow in a three-dimensional biological tissue environment because the cells grow while being attached to the surface of a culture container treated such that the cells are attached well to the surface of the culture container. Thus, two-dimensional and three-dimensional cell cultures show overall morphological differences, and in addition, the two-dimensional cell culture method has a problem in that it cannot accurately reflect the physiological environment of the living body in which cells grow in a three-dimensional environment because many complex life phenomena such as receptor expression, gene transcriptional regulation, cell migration, and cell apoptosis which occur through a typical two-dimensional cell culture are significantly different from those occurring in the actual tissue environment.

Indeed, when developing a therapeutic agent for a metabolic disease, such as obesity, diabetes, and atherosclerosis, drugs that showed good efficacy in initial in vitro experiments are significantly less effective in in vivo animal experiments, so that there are many difficulties in developing new drugs. In order to solve these problems, an in vitro model similar to an in vivo model capable of predicting the exact efficacy and toxicity of a drug from the early stage of therapeutic agent development is required.

Cell culture containers in the related art do not supply and circulate air smoothly due to spatial limitations during three-dimensional cell culture, so that it is difficult to apply the cell culture container to drug screening or toxicity tests because it is difficult to grow three-dimensional cells and form tissues of the cells sufficiently.

Therefore, in order to address these issues, there is a need for developing a technology for a cell culture container capable of two-dimensional and three-dimensional co-culture while being suitable for rapid growth of three-dimensional cells.

Further, there is a need for a three-dimensional cell culture container which can be compatible with existing cell culture plates which have been widely used.

DISCLOSURE

Technical Problem

The present invention has been devised to solve the aforementioned problems and an object thereof is to provide an insertable culture container and a kit for three-dimensional cell culture, and a three-dimensional cell co-culture method using the same, in which air required for a three-dimensional cell culture structure can be smoothly supplied since the cells are cultured at a position spaced apart from a bottom surface of the culture container, unlike the related art.

Further, an object of the present invention is to alleviate, when a membrane in the related art is used on the bottom surface, a problem in that only a part of an ingredient such as a protein can be supplied due to the limitation in pore size and a problem in that cells or supports inevitably make physical contact with the membrane, such that all ingredients can be supplied without any physical contact due to the special structure of a support of the present invention.

In addition, an object of the present invention is to enable a three-dimensional structure to be easily inserted, obtained, and removed by implementing the structure of a support which separately supports the three-dimensional structure on a culture container.

Furthermore, an object of the present invention is to enable a three-dimensional structure to be further easily inserted, obtained, and removed because the culture container according to the present invention is configured as an insert type and to replace the culture container according to the present invention conveniently and easily because an existing culture plate can continue to be used as it is.

An object of the present invention is to efficiently maintain the co-culture of two or more types of cells when a cell culture kit including the insertable culture container according to the present invention co-cultures the cells by supplying air and smoothly supplying nutrient ingredients in a culture medium due to the support structure optimized for the three-dimensional culture.

The three-dimensional cell culture method according to the present invention enables rapid cell growth and can regulate various sizes, and three-dimensionally cultured and differentiated cells can be applied to animal replacement tests and effectively used for drug screening or toxicity tests.

Further, an object of the present invention is to enable the culture container according to the present invention to be utilized as a container for three-dimensional cell culture and differentiation or tissue culture for restoring the function of damaged human tissues.

Technical Solution

To achieve the aforementioned objects, the insertable culture container for three-dimensional cell culture includes: a cylindrical side wall having open upper and lower portions; at least one hook protruding outward from the upper side of the side wall; and at least one support protruding inward from the lower side of the side wall.

The support may be located below a central portion of the side wall.

The at least one support may be disposed at equal intervals.

The container may have a cylindrical shape in which the upper side of the sidewall has a larger cross section than the lower side of the sidewall.

The ratio of a diameter of the upper portion of the side wall and a diameter of the lower portion of the side wall may be 3:1 to 1.2:1.

The distance from the side wall to the end of the support may be 15 to 30% of the diameter of the upper portion.

Another aspect of the present invention provides an insertable culture container kit for three-dimensional cell culture according to the present invention.

Specifically, an insertable culture container kit for three-dimensional cell culture is a kit for three-dimensional cell culture including an insertable culture container which includes a cylindrical side wall having open upper and lower portions; at least one hook protruding outward from the upper side of the side wall; and at least one support protruding inward from the lower side of the side wall and a plate into which the culture container is introduced, in which the plate includes at least one well recessed in one direction; and a connecting portion connecting the wells, and the insertable culture container is insertable into the well of the plate, the hook of the culture container is caught on the connecting portion of the plate, and a bottom surface of the well is spaced apart from a lower portion of the culture container.

A separation distance of the bottom surface of the well from the lower portion of the culture container may be 10 to 40% of a depth of the well.

Still another aspect of the present invention provides a method for co-culturing cells three-dimensionally using a kit for three-dimensional cell culture.

Specifically, the method for co-culturing three-dimensional cells according to the present invention includes: a preparation step of preparing a kit for three-dimensional cell culture including an insertable culture container which includes a cylindrical side wall having open upper and lower portions; at least one hook protruding outward from the upper side of the side wall; and at least one support protruding inward from the lower side of the side wall, and a plate into which the culture container is introduced, in which the plate includes at least one well recessed in one direction; and a connecting portion connecting the wells, the insertable culture container is insertable into the well of the plate, the hook of the culture container is caught on the connecting portion of the plate, and a bottom surface of the well is spaced apart from a lower portion of the culture container;

an inoculation step of inoculating a first cell inside the well of the plate;

an exchange step of removing a supernatant and at least partially exchanging a culture solution after culturing the first cell;

an insertion step of inserting the insertable culture container into the well of the plate; and a co-culture step of co-culturing cells by locating a three-dimensional structure inoculated with a second cell on the support.

Advantageous Effects

The insertable culture container and the kit for three-dimensional cell culture, and the three-dimensional cell co-culture method using the same according to the present invention are advantageous in that oxygen required for a three-dimensional cell culture structure can be smoothly supplied since the cells are cultured at a position spaced apart from a bottom surface of the culture container, unlike the related art.

Further, the insertable culture container and the kit for three-dimensional cell culture, and the three-dimensional cell co-culture method using the same according to the present invention are advantageous in that they alleviate, when a membrane in the related art is used on the bottom surface, a problem in that only a part of an ingredient such as a protein can be supplied due to the limitation in pore size and a problem in that cells or supports inevitably make physical contact with the membrane, such that all ingredients can be supplied without any physical contact due to the special structure of a support of the present invention.

The insertable culture container and the kit for three-dimensional cell culture, and the three-dimensional cell co-culture method using the same according to the present invention are advantageous in that they enable a three-dimensional structure to be easily inserted, obtained, and removed by implementing the structure of a support which separately supports the three-dimensional structure on a culture container.

In addition, the insertable culture container and the kit for three-dimensional cell culture, and the three-dimensional cell co-culture method using the same according to the present invention are advantageous in that they enable a three-dimensional structure to be further easily inserted, obtained, and removed due to the culture container configured as an insert type and to replace the culture container according to the present invention conveniently and easily because an existing culture plate can continue to be used as it is.

The insertable culture container and the kit for three-dimensional cell culture, and the three-dimensional cell co-culture method using the same according to the present invention are advantageous in that it is possible to efficiently perform three-dimensional cell culture and co-culture two or more types of cells due to the support structure optimized for the three-dimensional culture.

The three-dimensional cell culture method according to the present invention is advantageous in that it enables rapid cell growth and can regulate various sizes, and is more effective for drug screening or efficacy confirmation, toxicity tests, and the like as a biomimetic model or animal replacement test method.

Furthermore, the insertable culture container according to the present invention is advantageous in that it can be utilized as a container for three-dimensional cell culture or tissue culture for restoring the function of damaged human tissues.

MODES OF THE INVENTION

Hereinafter, one preferred embodiment of the present invention for an insertable culture container and a kit for three-dimensional cell culture, and a three-dimensional cell co-culture method using the same according to the present invention will be described in detail with reference to the accompanying drawings. The present invention can be better understood by the following examples, and the following examples are provided only for the purpose of illustrating the present invention and are not intended to limit the scope of protection, which is limited by the attached claims.

Figure 1:
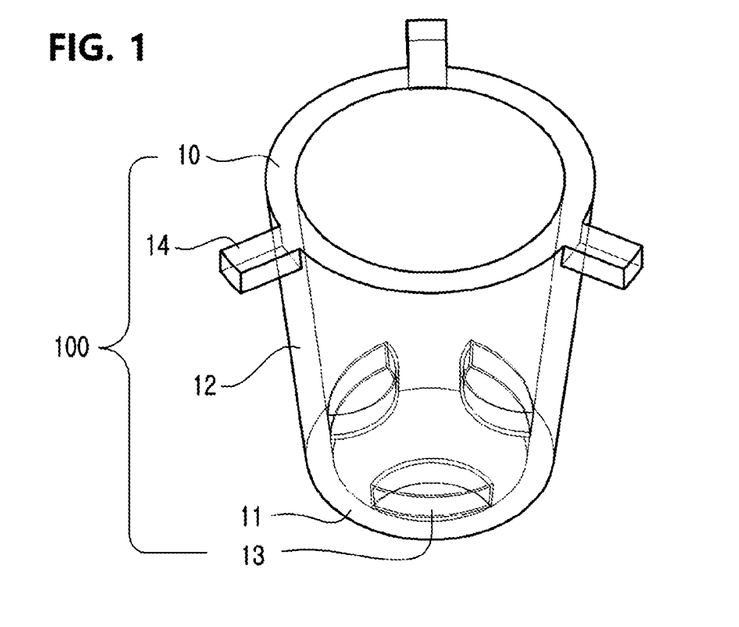
FIG. 1 is a perspective view illustrating an insertable culture container for three-dimensional cell culture of the present invention
Figure 2:
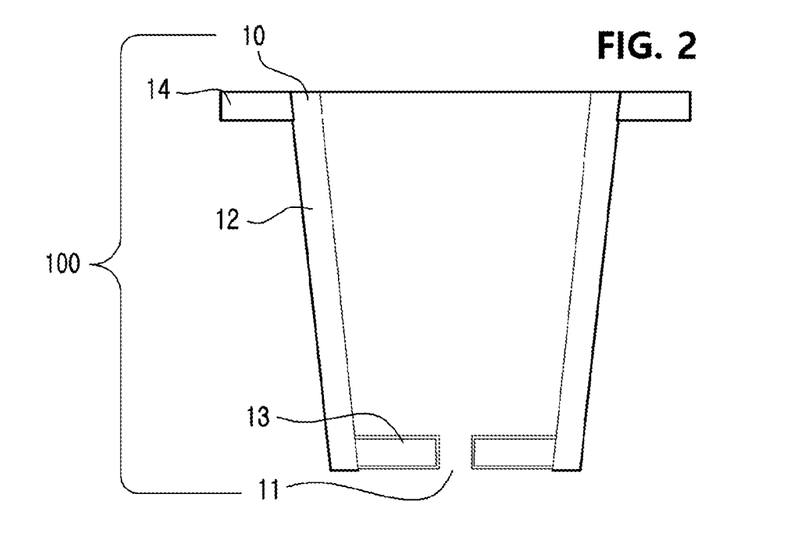
FIG. 2 is a cross-sectional view illustrating the insertable culture container for three-dimensional cell culture of the present invention
Figure 3:
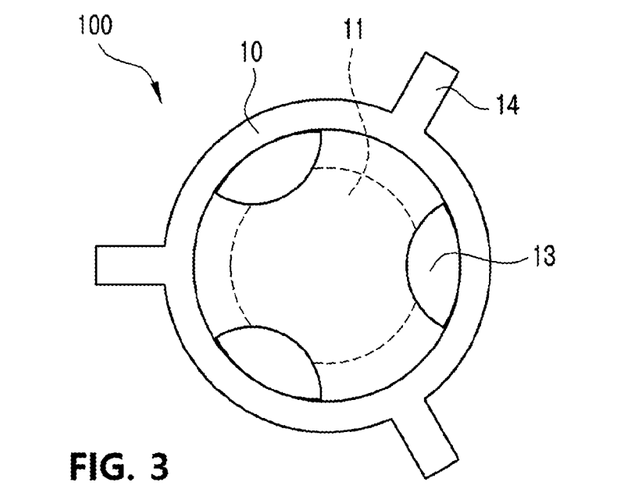
FIG. 3 is a plan view illustrating the insertable culture container for three-dimensional cell culture of the present invention

As illustrated in FIGS. 1 to 3, an insertable culture container 100 for three-dimensional cell culture of the present invention may include an upper portion 10, a lower portion 11, a side wall 12, and a support 13.

First, the upper portion 10 means an open upper portion for introducing a three-dimensional structure, and along with the lower portion 11 and the side wall 12, may form a basic structure having a columnar shape which is opened vertically.

The lower portion 11 is formed in an open form so as to co-culture heterogeneous cells with a culture solution.

The ratio of a diameter of the upper portion 10 and a diameter of the lower portion may be 3:1 to 1.2:1, preferably 2:1 to 1.5:1, and more preferably 1.8:1 to 1.6:1, which is effective. In this range, an inclined sidewall that maximizes the interaction between the culture solution and the heterogeneous cells while enabling a three-dimensional structure to be inserted and removed into/from the upper portion, and is optimal for securing a structural bonding stability with the well, is formed.

When the ratio is more than 3:1, the efficiency of circulating and supplying air from the lower portion, co-culturing two or more types of cells, and the like may remarkably deteriorate, and when the ratio is less than 1.2:1, the ease with which the three-dimensional structure is inserted and removed into/from the upper portion may be lowered, or the structural bonding stability with the lower well may deteriorate.

The side wall 12 is configured to extend from the upper portion 10 to the lower portion 11, protects the three-dimensional structure, and forms a base surface for forming the support 13.

Further, the support 13 is formed to protrude inward from the lower side of the side wall 12, and the number of supports 13 is preferably 2 to 5, more preferably 3 to 4, and most preferably 3, which is effective. There are problems in that when the number is less than 2, it is virtually impossible to support a three-dimensional cell structure, and when the number is more than 5, the connection space with the actual lower well is excessively narrow compared to the open space of the lower portion 12 due to the supports, so that the efficiency of circulating and supplying air, co-culturing two or more types of cells, and the like remarkably deteriorates.

The at least one support is characterized by being disposed at equal intervals.

The support is characterized by being located below a central portion of the side wall.

The support 13 is spaced apart from the upper portion 10, and is located at a height which is preferably 0 to 40%, more preferably 5 to 25%, and most preferably 5 to 10% of the side wall 12 from the lower open end 11, which is effective. There is a problem in that when the support 13 is located at a height which is more than 40% of the side wall 12 from the lower open end 11, it is difficult to co-culture a three-dimensional cell structure which is put on the support 13 and other cells contained in the well.

The distance from the side wall 12 to the end of the support 13 is preferably 15 to 30%, more preferably 20 to 25%, and most preferably 22 to 23% of the diameter of the upper portion 10, which is effective. There are problems in that when the distance is less than 15%, it is difficult to stably support a three-dimensional cell structure, and when the distance is more than 30%, the effect of being spaced apart from the lower portion 11 of the support 13 is lowered, that is, cell growth is adversely affected because it is difficult to circulate and supply air smoothly.

The support 13 may extend to the lower portion 11. Since the support 13 is formed along the side wall 12 from the lower portion 11, there is an advantage in that the manufacturing process is simple and economic feasibility is high because injection molding as one body is facilitated. In addition, the support 13 is formed in a columnar form along the side wall 12, and thus has higher stability and durability.

Furthermore, the hook 14 may be formed protruding outward from the upper side of the side wall 12.

The upper portion 10, the lower portion 11, the side wall 12, the support 13, and the hook 14 may be formed of any material applied to cell culture, such as polystyrene (PS), polypropylene (PP), polyethylene (PE), polycarbonate (PC), and glass, and the side wall 12 and the support 13, which are formed of the same material, are suitable for a durable and integral side wall which is easily injection-moldable.

Figure 4:
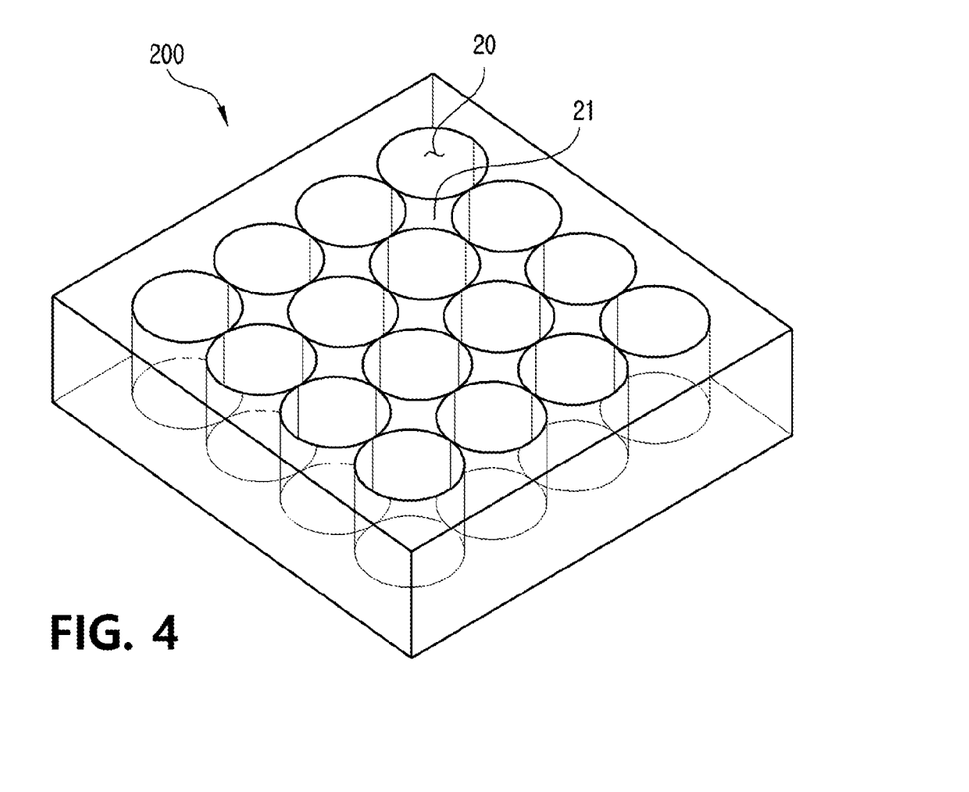
FIG. 4 is a perspective view illustrating a cell culture plate of an insertable culture container kit for three-dimensional cell culture of the present invention
Figure 5:
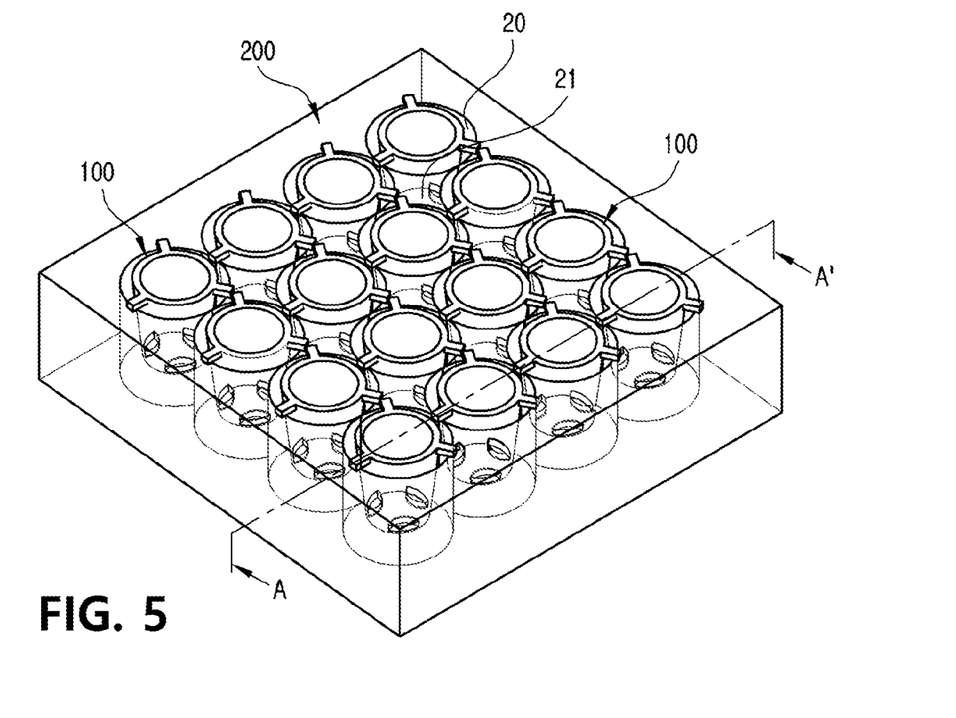
FIG. 5 is a perspective view illustrating a state in which an insertable culture container is introduced onto a plate in the insertable culture container kit for three-dimensional cell culture of the present invention
Figure 6:
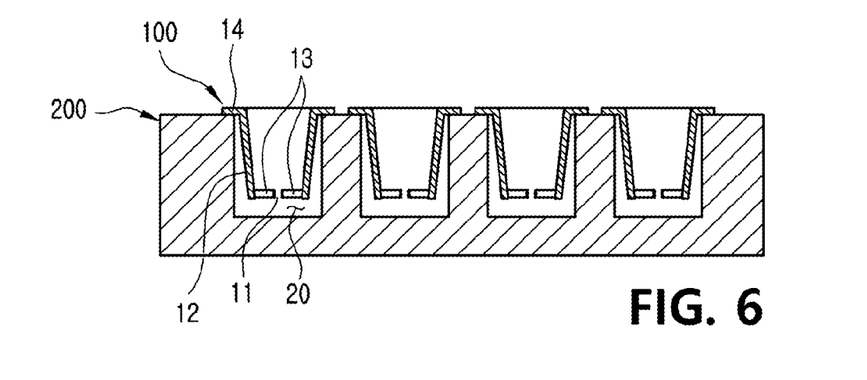
FIG. 6 is a cross-sectional view illustrating a state in which the insertable culture container is introduced onto the plate in the insertable culture container kit for three-dimensional cell culture of the present invention

Next, as illustrated in FIGS. 4 to 6, the insertable culture container kit for three-dimensional cell culture of the present invention may include an insertable culture container 100 for three-dimensional cell culture and a cell culture plate 200, that is, a plate 200 and an insertable culture container 100.

Here, the plate 200 may include: at least one well 20 recessed in one direction; and a connecting portion 21 connecting the wells 20.

As illustrated in FIGS. 5 and 6, an insertable culture container 100 may be introduced into the well 20 of the plate 200. When introduced, the hook 14 is caught on the connecting portion 21, and thus serves to support the insertable culture container 100.

A bottom surface of the well 20 is spaced apart from the lower open end 11, and a separation distance of the bottom surface of the well from the lower open end 11 is preferably 10 to 40%, more preferably 15 to 25%, and most preferably 15 to 20%, of a depth of the well, which is effective. There are problems in that when the distance is less than 10%, it is difficult to smoothly circulate and supply air to cells in the lower portion, and when the distance is more than 40%, it is difficult to co-culture a three-dimensional cell structure which is put on the support 13 and other cells contained in the well.

The number of wells 20 formed on the plate 200 is not limited, and the plate 200 may be configured to have various numbers of wells such as 16 wells and 96 wells.

Figure 7:
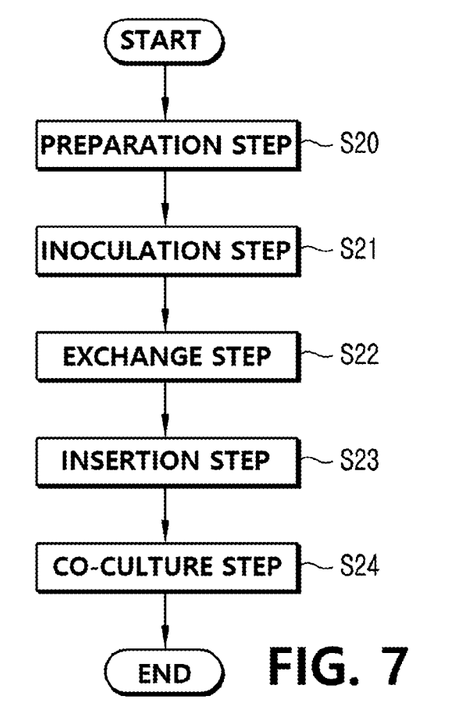
FIG. 7 is a flowchart sequentially illustrating a three-dimensional cell co-culture method of the present invention

The three-dimensional cell co-culture method of the present invention may include: a preparation step S20; an inoculation step S21, an exchange step S22; an insertion step 23; and a co-culture step S24. This is a method which can effectively co-culture a first cell and a second cell using the insertable culture container structure for three-dimensional cell culture of the present invention.

First, the preparation step S20 is a step of preparing a kit for three-dimensional cell culture, which includes an insertable culture container according to the present invention and a plate into which the culture container is introduced.

The inoculation step S21 is a step of inoculating the first cell inside the well. That is, the first cell and the culture solution may be inoculated inside the well.

Here, the first cell may be any cell that can be co-cultured with the second cell, but may be precisely an adherent cell, and may be at least one such as a mesenchymal cell or mesenchymal stem cell, a pre-adipocyte, an adipocyte, a smooth muscle cell (SMC), or a macrophage.

The exchange step S22 is a step of removing a supernatant and at least partially exchanging a culture solution after culturing the first cell. Co-culture efficiency may be increased by removing a supernatant generated by culturing the first cell from the culture solution in the well and exchanging a part or all of the culture solution.

The insertion step S23 is a step of inserting the insertable culture container into the well of the plate.

The co-culture step S24 is a step of co-culturing cells by locating a three-dimensional structure inoculated with a second cell on the support of the culture container. Here, the three-dimensional structure is preferably in the form of a bead or support.

Here, the second cell may be a culturable eukaryotic cell, and more specifically, at least one of an epithelial cell, a fibroblast, an osteoblast, a chondrocyte, a hepatocyte, an umbilical cord blood cell, an umbilical cord mesenchymal stem cell (UCMSC), an adipose-derived mesenchymal stem cell (AMSC), or a bone marrow-derived mesenchymal stem cell (BMMSC).

Finally, the exchange step S24 is a step of exchanging the culture solution at an interval of 1 to 5 days after the co-culture step S24. More preferably, it is effective to exchange the culture solution at an interval of 2 to 3 days. This is to ensure the continuous growth of cells or tissues by supplying nutrient ingredients required for cell culture by and removing cell survival inhibitors produced during the culture.

Example 1) Manufacture and Sterilization of Culture Container

As an example of the present development, a culture container was manufactured using a 3D printing technique in which layers are laminated one by one by an arbitrary solid freeform fabrication (SFF) method using a rapid prototyping (RP) device, and sterilization was performed using an electron beam accelerator.

Example 2) First Cell Culture

As an experiment for measuring the effect of three-dimensional cell culture using the insertable culture container kit for three-dimensional cell culture of the present invention, an experiment was performed under the following conditions.

Cells: 3T3-L1 (pre-adipocyte)($2.45 \times 10^6$ cells/5 mL/Tube), adipose-derived mesenchymal stem cell (ADMSC)

Culture period: 7 day culture

Cell counting: cell counting on days 0, 3, and 7

Alginate mixture: 1.3% concentration

The first cell was 3T3-L1(pre-adipocyte), and specifically, cryopreserved first cells were thawed in a constant-temperature water bath at 37° C. and transferred to a 15-ml tube, and then a basal medium (DMEM+1% antibiotics) was added thereto and centrifuged at 1,500 RPM for 5 minutes to remove a supernatant, and after cryopreservation solution ingredients were completely removed by adding the basal medium again and repeating the previous method, cells were inoculated along with a medium including DMEM+1% antibiotics+10% FBS into a 100-mm culture dish and cultured in a 5% carbon dioxide incubator at 37° C. and when the cells were sufficiently proliferated after 4 to 5 days, the cells were inoculated at a concentration of $1 \times 10^3$ per well of the culture container by treating the cells with 0.05% trypsin-EDTA.

Example 3) Manufacture of Bead Including Second Cell

The second cell was an adipose-derived mesenchymal stem cell (ADMSC), and a three-dimensional structure inoculated with the second cell was manufactured in the form of a bead.

The bead was manufactured by a method including: a melting step of introducing a culture solution, alginate, and gelatin into a tube and melting the resulting solution at 65° C.; a stirring step of lowering the temperature of the tube to 37° C., introducing the second cell ($2.45 \times 10^6$ cells/5 mL/Tube) into the tube, and stirring the tube at 500 RPM for 2 minutes; and a manufacturing step of making the mixture in the tube in the form of a bead and manufacturing the bead by putting the mixture in a calcium chloride solution for cross-linking.

After the stirring, bubbles were removed at 1500 RPM through centrifugation. In the manufacturing step, the concentration of the calcium chloride solution was set at 5%.

A three-dimensional structure in the form of a bead inoculated with the second cell was manufactured by washing the cross-linked bead with phosphate buffered saline (PBS) and putting the bead into a culture solution containing 10% fetal bovine serum and culturing in a 5% carbon dioxide incubator at 37° C.

Example 4) Manufacture of Support and Sterilization Process

A support was manufactured using polycaprolactone. First, after polycaprolactone was introduced into a tube and a pressure of 650 to 730 kPa was applied thereto, a three-dimensional support was manufactured using the suction function of an air controller, and a sterilization process was performed using electron beam acceleration.

Example 5) Three-Dimensional Cell Culture Using Support Including Second Cell For a three-dimensional cell culture using a support including a second cell, after 25 μl of the second cells was each inoculated onto 4 drop supports, a three-dimensional structure in the form of a support inoculated with the second cells was manufactured by culturing the second cell for 1 hour, adding 1 ml of a medium thereto, and culturing the second cells under 37° C. and 5% carbon dioxide conditions.

Figure 8:
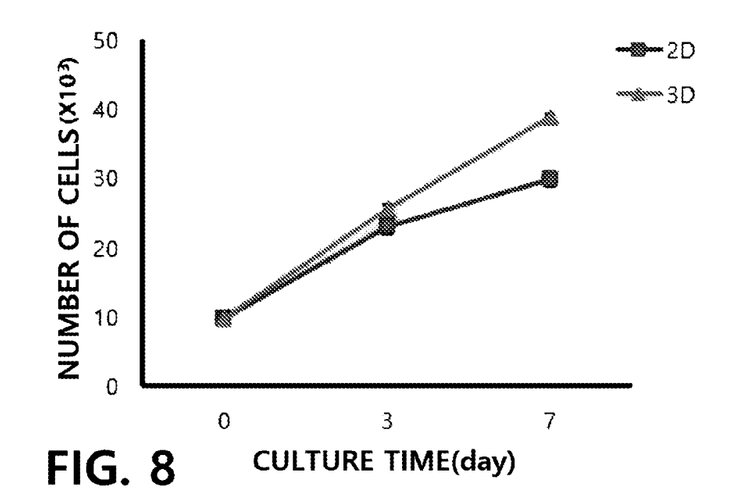
FIG. 8 is a graph illustrating experimental results in which three-dimensional cell culture is performed by the insertable culture container kit for three-dimensional cell culture of the present invention

As illustrated in FIG. 8, it can be seen that for the three-dimensional cell culture performed using the insertable culture container of the present invention, as the culture time elapses, the number of cells are is not decreased, but increased, unlike a second-dimensional cell culture using a general culture container. That is, it could be confirmed in an actual experiment that the three-dimensional cell culture could be performed more sustainably with the culture container of the present invention.

While preferred embodiments of the present invention have been described, the present invention is susceptible to various changes, modifications and equivalents. It is clear that the embodiments of the present invention can be appropriately modified and equally applied. Therefore, the aforementioned description should be construed as not limiting the scope of the present invention defined by the following claims.

EXPLANATION OF REFERENCE NUMERALS AND SYMBOLS

100: Insertable culture container for three-dimensional cell culture
10: Upper portion
11: Lower portion
12: Side wall
13: Support
14: Hook
200: Cell culture plate
20: Well
21: Connecting portion

INDUSTRIAL APPLICABILITY

The present invention relates to an insertable culture container and a kit for three-dimensional cell culture, and a three-dimensional cell co-culture method using the same, and is industrially applicable.

The invention claimed is:

1. An insertable culture container for three-dimensional cell culture comprising: a cylindrical side wall having open upper and lower portions; at least one hook protruding outward from an upper side of the cylindrical side wall; and a plurality of supports protruding inward from a lower side of the cylindrical side wall and provided to support a three-dimensional structure inoculated with cells,
   wherein the plurality of supports are spaced apart from each other and spaced apart from a center of an inner space surrounded by the cylindrical side wall,
   wherein distances from the cylindrical side wall to ends of the plurality of supports are 15 to 30% of a diameter of the upper portion, and
   wherein the open lower portion of the container does not comprise a membrane.

2. The insertable culture container of claim 1, wherein the plurality of supports are located below a central portion of the cylindrical side wall.

3. The insertable culture container of claim 1, wherein the plurality of supports are disposed at equal intervals.

4. The insertable culture container of claim 1, wherein the insertable culture container has a cylindrical shape, in which the upper side of the cylindrical sidewall has a larger cross section than the lower side of the cylindrical sidewall.

5. A kit for three-dimensional cell culture comprising the insertable culture container of claim 1 and a plate into which the insertable culture container is inserted, wherein the plate includes a plurality of wells recessed in one direction;
   a connecting portion connecting the plurality of wells, wherein the insertable culture container is insertable into the plurality of wells of the plate such that the at least one hook of the culture container is caught on the connecting portion of the plate; and
   bottom surfaces of the plurality of wells spaced apart from a lower portion of the insertable culture container.

6. The kit of claim 5, wherein a separation distance of the bottom surfaces of the plurality of wells from the lower portion of the insertable culture container is 10 to 40% of depths of the plurality of wells.

7. A three-dimensional cell co-culture method comprising: a preparation step of preparing the kit of claim 5; an inoculation step of inoculating a first cell inside the plurality of wells of the plate; an exchange step of removing a supernatant and at least partially exchanging a culture solution after culturing the first cell; an insertion step of inserting the insertable culture container into the plurality of well of the plate; and a co-culture step of co-culturing cells by locating a three-dimensional structure inoculated with a second cell on the plurality of supports.

\* \* \* \* \*